United States Patent [19]

Bissolino et al.

[11] Patent Number: 5,348,952
[45] Date of Patent: Sep. 20, 1994

[54] β-LACTAM DERIVATIVES OF THE CEPHEM SULPHONE TYPE

[75] Inventors: Pierluigi Bissolino, Lomellina; Marco Alpegiani, Milan; Ettore Perrone, Boffalora Ticino; Piergiuseppe Orezzi, Milan; Giuseppe Cassinelli, Voghera; Giovanni Franceschi, Milan, all of Italy

[73] Assignee: Farmitalia Carlo Erba S.R.L., Milan, Italy

[21] Appl. No.: 853,745

[22] PCT Filed: Dec. 14, 1990

[86] PCT No.: PCT/EP90/02189

§ 371 Date: Jun. 12, 1992

§ 102(e) Date: Jun. 12, 1992

[87] PCT Pub. No.: WO91/09036

PCT Pub. Date: Jun. 27, 1991

[30] Foreign Application Priority Data

Dec. 15, 1989 [GB] United Kingdom ............... 8928373

[51] Int. Cl.⁵ ................. C07D 501/20; A61K 31/545
[52] U.S. Cl. .................... 514/202; 514/204; 540/222; 540/226; 540/223
[58] Field of Search ............. 540/226, 227, 221; 514/201, 202, 204

[56] References Cited

U.S. PATENT DOCUMENTS

| | | |
|---|---|---|
| 3,852,282 | 12/1974 | Dolfini . |
| 4,163,743 | 8/1979 | Wasserman et al. . |
| 4,368,203 | 1/1983 | Okamura et al. . |
| 4,377,590 | 3/1983 | Myers . |
| 4,486,411 | 12/1984 | Hamanaka . |
| 4,499,017 | 2/1985 | Pirie et al. . |
| 4,610,824 | 9/1986 | Truner . |
| 4,845,088 | 7/1989 | Doherty et al. . |
| 5,077,286 | 12/1991 | Bissolini et al. ............... 540/221 |
| 5,132,301 | 7/1992 | Doherty et al. ............... 540/221 |
| 5,258,377 | 11/1993 | Maiti et al. ............... 514/201 |

FOREIGN PATENT DOCUMENTS

| | | |
|---|---|---|
| 0118567 | 9/1984 | European Pat. Off. . |
| 2250759 | 6/1975 | France . |
| 2254575 | 7/1975 | France . |

OTHER PUBLICATIONS

Chemical Abstract, vol. 82, No. 7, Feb. 17, 1975, (Columbus, Ohio, US), see p. 444, abstract 43443g, & JP, A, 7448690 (Yamanouchi Pharmaceutical Co., Ltd) May 11, 1974.

Primary Examiner—Nicholas S. Rizzo
Attorney, Agent, or Firm—Oblon, Spivak, McClelland, Maier & Neustadt

[57] ABSTRACT

Cephalosporins of the formula (I):

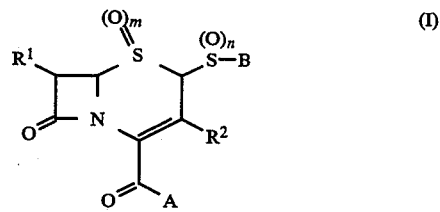

wherein m is one or two; n is zero, one or two; A and B are organic residues; and $R_1$ and $R_2$ are halogen or hydrogen atoms or organic groups are endowed with elastase inhibitory activity. Two processes for their preparation starting from the corresponding 4-acyl cephem are also provided.

5 Claims, No Drawings

β-LACTAM DERIVATIVES OF THE CEPHEM SULPHONE TYPE

The present invention relates to new cephalosporins, their preparation and to pharmaceutical and veterinary compositions containing them.

The compounds disclosed in the present invention feature the simultaneous presence on the cephem skeleton of an acyl group at C-4 and a sulphenyl, sulphinyl or sulphonyl group at C-2.

According to the invention there are provided cephalosporins of formula (I) and the pharmaceutically and veterinarily acceptable salts thereof:

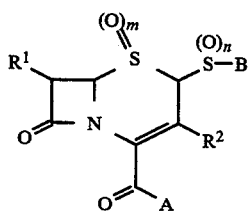

(I)

wherein m is one or two; n is zero, one or two;

A and B are both or each independently an organic radical selected from $C_1$-$C_{12}$ straight or branched alkyl; $C_2$-$C_{10}$ alkenyl; $C_2$-$C_{10}$ alkynyl; $C_6$-$C_{10}$ aryl; $C_3$-$C_8$ cycloalkyl; $C_5$-$C_8$ cycloalkenyl; aralkyl, aralkenyl, aralkynyl or (cycloalkyl)alkyl wherein the aryl, cycloalkyl, alkyl, alkenyl and alkynyl groups are as defined above; a first 5- or 6-membered, saturated or unsaturated, heterocyclyl ring, containing at least one heteroatom chosen from O, S and N, which is optionally fused to a second said 5- or 6-membered heterocyclyl group or to a $C_3$-$C_8$ cycloalkyl group; or heterocyclylalkyl, heterocyclylalkenyl or heterocyclylalkynyl wherein the heterocyclyl, alkyl, alkenyl and alkynyl groups are as defined above; wherein each of the said organic radicals is unsubstituted or substituted by one or more atom or group selected from;

halo;
hydroxy;
nitro;
azido;
diazo;
amino —$NH_2$, or —NHR′ or NR′R″ wherein R′ and R″, being the same or different, are $C_1$-$C_7$ straight or branched alkyl, phenyl or benzyl;
formyl—CHO;
mercapto—SH, or SR′ wherein R′ is as defined above;
cyano;
carboxy —$CO_2H$, or $CO_2R'$ wherein R′ is as defined above;
sulpho —$SO_3H$;
acyl C(O)R′ wherein R′ is as defined above or trifluoroacetyl C(O)$CF_3$;
carbamoyl —$CONH_2$, N-methylcarbamoyl —$CONHCH_3$ or N-(carboxymethyl)carbamoyl —CONH—$CH_2CO_2H$;
carbamoyloxy —$OCONH_2$;
acyloxy OC(O)R′ wherein R′ is as defined above or formyloxy OC(O)H;
alkoxycarbonyl or benzyloxycarbonyl —C(O)OR′ wherein R′ is as defined above;
alkoxycarbonyloxy or benzyloxycarbonyloxy OC(O)R′ wherein R′ is as defined above;
alkoxy, phenoxy or benzyloxy —O—R′ wherein R′ is as defined above;
alkylthio, phenylthio or benzylthio —S—R′ wherein R′ is as defined above;
alkylsulphinyl, phenylsulphinyl or benzylsulphinyl S(O)R′ wherein R′ is as defined above;
alkylsulphonyl, phenylsulphonyl or benzylsulphonyl $S(O)_2R'$ wherein R′ is as defined above;
acylamino —NHC(O)R′″ or —NHC(O)OR′″ wherein R′″ is $C_1$-$C_7$ straight or branched alkyl, phenyl, benzyl, $CH_2CH_2CO_2H$ or $CH_2CH_2CH_2CO_2H$;
sulphonamido —NH—$SO_2R'$ wherein R′ is as defined above;
guanidino —NHC(=NH)$NH_2$;
$C_1$-$C_4$ alkyl, $C_2$-$C_4$ alkenyl or alkynyl;
$C_3$-$C_6$ cycloalkyl; and
substituted $C_1$-$C_4$ alkyl selected from chloromethyl, fluoromethyl, difluoromethyl, trifluoromethyl, aminomethyl, azidomethyl, cyanomethyl, carboxymethyl, carbamoylmethyl, carbamoyloxymethyl, hydroxymethyl, $C_3$-$C_4$ alkoxycarbonylmethyl, guanidinomethyl;

$R^1$ represents:
(1) hydrogen, chloro, fluoro, bromo or iodo;
(2) A as defined above;
(3) an ether —O—A wherein A is as defined above;
(4) a thioether, sulphoxide or sulphone —$S(O)_nA$ wherein n is either 0, 1 or 2 and wherein A is as defined above;
(5) acyloxy —OC(O)A wherein A is as defined above;
(6) sulphonyloxy —O—$SO_2A$ wherein A is as defined above; or
(7) acylamino —NHC(O)A wherein A is as defined above or acylamino —NH—Z wherein Z is a mono, di- or tripeptide composed of D or L α-aminoacids chosen from Ala, Gly, Val, Leu, Ile, Phe and Pro, and with the terminal amino group either free, or acylated by a group —C(O)R′″ or —C(O)OR′″ wherein R′″ is as defined above;

$R^2$ represents:
(1) A as defined above;
(2) chloro or fluoro or hydrogen;
(3) an oxy group —O—A, wherein A is as defined above;
(4) a sulphenyl, sulphinyl or sulphonyl group —$S(O)_nA$, wherein n and A are as defined above;
(5) an acyl group —C(O)A, —C(O)OA or —$CO_2H$ wherein A is as defined above;
(6) an oxymethyl group —$CH_2$—O—A wherein A is as defined above;
(7) a thiomethyl group or a derivative thereof of formula —$CH_2S(O)_nA$ wherein n and A are as defined above;
(8) an acyloxymethyl group —$CH_2OC(O)A$ or —$CH_2$—O—Z, wherein A and Z are as defined above;
(9) an acylthiomethyl group —$CH_2SC(O)A$ wherein A is as defined above;
(10) an aminomethyl group —$CH_2$—N(A)A′ wherein A is as defined above and A′, being the same or different, is as defined for A; or A and A′ taken together with the nitrogen atom to which they are attached represent a heterocyclic ring;

(11)

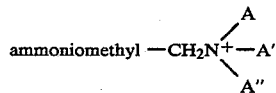

wherein A and A' are as defined above and A", being the same or different, is as defined for A; or A is alkyl and A' and A" together with the nitrogen atom to which they are attached represent a heterocyclic ring; or A, A' and A" together with the nitrogen atom to which they are attached represent an aromatic heterocyclic ring; or

(12) acylaminomethyl —CH$_2$NH—C(O)A or —CH$_2$—NH—Z wherein A and Z are as defined above.

The present invention provides the salts of those compounds of formula (I) that have salt-forming groups, especially the salts of the compounds having a carboxylic group, a basic group (e.g. an amino or guanidino group), or a quaternary ammonium group. The salts are especially physiologically tolerable salts, for example alkali metal and alkaline earth metal salts (e.g. sodium, potassium, lithium, calcium and magnesium salts), ammonium salts and salts with an appropriate organic amine or amino acid (e.g. arginine, procaine salts), and the addition salts formed with suitable organic or inorganic acids, for example hydrochloric acid, sulphuric acid, carboxylic and sulphonic organic acids (e.g. acetic, trifluoroacetic, p-toluensulphonic acid). Some compounds of formula (I) which contain a carboxylate and an ammonium group may exist as zwitterions; such salts are also part of the present invention.

The present invention encompasses all the possible stereoisomers and tautomers, as well as their racemic or optically active mixtures. However, the configurations depicted in formula (I') are particularly preferred

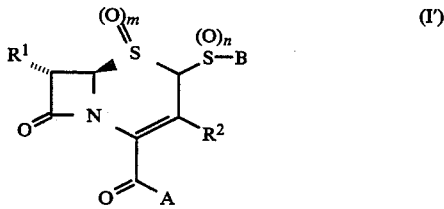

wherein m is one or two; n is zero, one or two;

A is methyl or $C_2$–$C_{10}$ straight or branched alkyl, alkenyl, alkynyl; $C_3$–$C_8$ cycloalkyl; dimethylphenyl, diphenylmethyl; phenyl or benzyl; wherein the alkyl, alkenyl, alkynyl, cycloalkyl, phenyl and benzyl groups are either unsubstituted or substituted by fluoro, chloro, carboxy, $C_1$–$C_4$ alkoxycarbonyl, carbamoyl, carbamoyloxy, methylsulphonyl, diazo, hydroxy, methoxy, ethoxy, tertbutoxy, benzyloxy, acetoxy, pivaloyloxy, benzoxy or phenylacetoxy;

B is (1') optionally substituted $C_1$–$C_5$ straight or branched alkyl or alkenyl or $C_1$–$C_6$ cycloalkyl;
(2') optionally substituted phenyl;
(3') optionally substituted aralkyl; or
(4') an optionally substituted first 5- or 6-membered saturated or unsaturated heterocyclic ring, containing one or more heteroatoms selected from O, S, N, optionally fused to a second said 5- or 6-membered carbocyclic or heterocyclic ring, the substituents for the groups defined under (1')–(4') being selected from hydroxy, $C_1$–$C_3$ alkoxy, phenoxy, benzyloxy, benzhydryloxy, methylthio, carboxy, carboxymethyl, carboxyethyl, carboxypropyl, carboxymethylthio, carbamoyl, carbamoylmethyl, amino, acetamido, formamido, dimethylamino, diethylamino, dimethylaminoethyl, nitro, cyano, sulpho, sulphamoyl, tetrazolyl, formimidoyl, ureido, chloro, fluoro, bromo, oxo, $C_1$–$C_5$ alkyl, vinyl and allyl;

$R^1$ is hydrogen or
(1') chloro, fluoro or bromo;
(2') $C_1$–$C_4$ alkyl, 1-(hydroxy)ethyl, 1-(benzyloxy)ethyl, 1-(benzyloxycarbonyloxy)ethyl, 1-(phenylacetoxy)ethyl, 2-fluoro-1-hydroxyethyl, isopropyl, phenyl, benzyl or allyl;
(3') methoxy, ethoxy, isopropoxy, phenoxy or benzyloxy;
(4') methylthio;
(5') formyloxy, acetoxy or phenylacetoxy;
(6') mesyloxy or tosyloxy;
(7') formamido, acetamido, fluoroacetamido, trifluoroacetamido or chloroacetamido;
(8') $R^V$-Ala-NH, wherein $R^V$ is either acetyl, tert-butoxycarbonyl, benzoxycarbonyl or HOOC—CH$_2$CH$_2$C(O)—;
(9') $R^V$-Val-NH wherein $R^V$ is as defined above; or
(10') Val-Pro-NH, Lys-NH or Ala-Ala-Pro-NH, wherein the terminal amino group of Val, Lys or Ala respectively or the α-amino group of Lys is either free or acylated with a group $R^V$ as defined above;

$R^2$ is either hydrogen or
(1') methyl, chloromethyl, bromomethyl, benzyl, ethyl, propyl or phenyl;
(2') chloro;
(3') methoxy or benzyloxy;
(4') methylthio;
(5') formyl, acetyl, benzoyl, carboxy, methoxycarbonyl, ethoxycarbonyl, tert-butoxycarbonyl or benxyloxycarbonyl;
(6') methoxymethyl, ethoxymethyl, isopropoxymethyl, benzyloxymethyl, phenoxymethyl or 3-pyridyloxymethyl, wherein the phenyl and pyridyl rings are either unsubstituted or substituted by one group or two groups which are the same or different, the said group or groups being chosen from hydroxy, carboxy, amino and $C_1$–$C_4$ alkoxycarbonyl;
(7') methylthiomethyl, phenylthiomethyl, methylsulphonylmethyl, phenylsulphynylmethyl or phenylsulphonyl methyl;
(8') —CH$_2$—S—Het wherein Het is a heterocyclic ring, preferably chosen from:

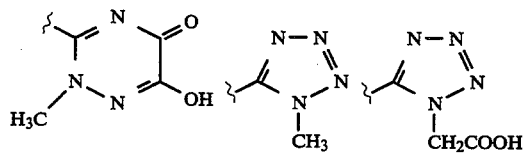

-continued

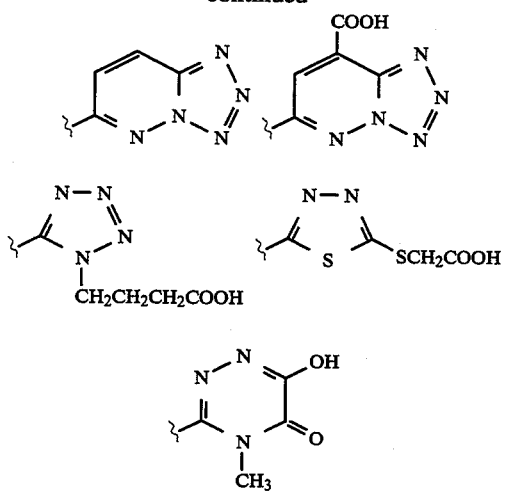

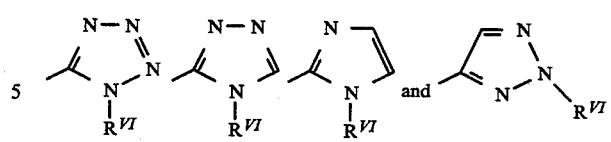

wherein $R^{VI}$ is hydrogen, methyl, carboxymethyl, 2-carboxyethyl, 3-carboxypropyl, 3-benzhydryloxycarbonylpropyl, 2-dimethylaminoethyl, 2-sulphoethyl, ethyl, propyl, phenyl or benzyl;

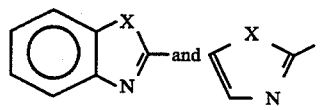

wherein X is oxygen, sulphur or $NR^{VII}$, $R^{VII}$ being hydrogen, methyl, phenyl or carboxymethyl;

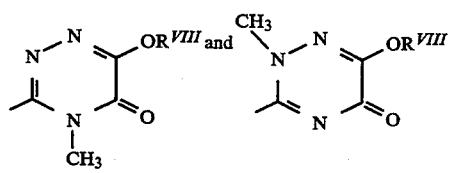

wherein $R^{VIII}$ is hydrogen, methyl, benzyl or benzhydryl; and

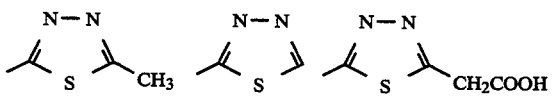

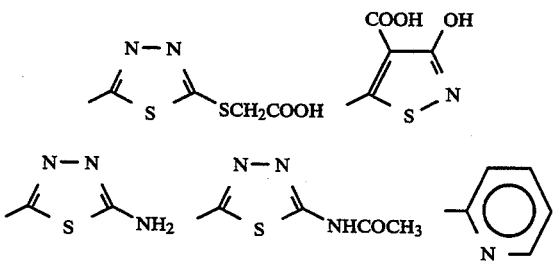

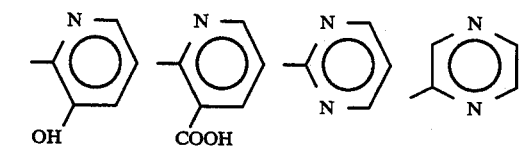

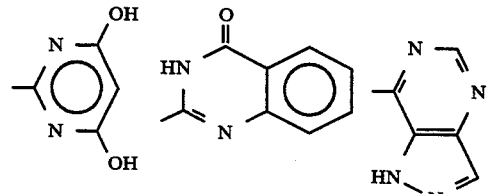

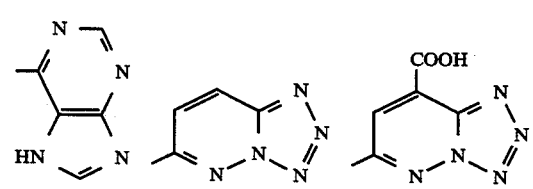

(9') acetoxymethyl, benzoxymethyl, phenylacetoxymethyl or $C_3$–$C_6$ alkanoyloxymethyl, each of which is either unsubstituted or substituted by one or more groups selected from carboxy, hydroxy and $C_1$–$C_3$ alkoxy;

(10') trialkylammoniomethyl wherein the alkyl group is chosen from methyl, ethyl, propyl; N-methylpyrrolidiniomethyl, N-methylpiperidiniomethyl and N-methylmorpholiniomethyl;

(11') pyridiniomethyl which is either unsubstituted or substituted on the heterocyclic ring by fluoro, chloro, methoxy, hydroxy, carboxy or carbamoyl; and the pharmaceutically and veterinarily acceptable salts thereof.

Still more preferred are compounds of formula (I') in which n is zero, one or two; m is one or two;

A is selected from hydrogen, methyl, ethyl, tert-butyl, neo-pentyl, benzyl, 1-phenylethyl, dimethylphenyl, diphenylmethyl, propenyl, phenylethenyl, cyclopentyl, 1-carboxycyclopentyl, diazomethyl, chloromethyl, hydroxymethyl, methoxymethyl, acetoxymethyl and pivaloyloxymethyl;

B is (1'') methyl, ethyl, propyl, isopropyl, allyl; carboxymethyl, 2-carboxy-2-aminoethyl, cyclopropyl, cyclopentyl, ethoxycarbonylmethyl, 2-carboxyethyl, 2-sulphoethyl or 1,2-dicarboxyethyl;

(2'') phenyl, 2-methoxyphenyl, 3-methoxyphenyl, 4-methoxyphenyl, 4-fluorophenyl, 4-nitrophenyl, 4-hydroxyphenyl, 4-carbamoylphenyl, 4-aminophenyl, 4-acetamidophenyl, 2-acetamidophenyl, 2-carboxyphenyl, 3-carboxyphenyl, 4-carboxyphenyl, 4-benzhydryloxycarbonylphenyl, 4-tert-butoxycarbonylphenyl, 3-carboxy-4-nitrophenyl, pentafluorophenyl, 4-carboxymethylphenyl or 4-sulphophenyl;

(3'') benzyl, p-carboxybenzyl, p-tert-butoxycarbonylbenzyl, m-carboxybenzyl, o-carboxybenzyl, p-benzhydryloxycarbonylbenzyl or p-sulphobenzyl;

(4'') an heterocyclic ring chosen from:

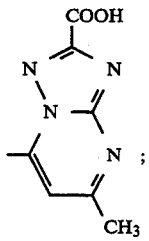

R[1] is hydrogen, chloro, bromo, fluoro, methoxy, formamido, acetamido, trifluoroacetamido, methyl, ethyl, propyl, isopropyl, allyl, 1-(hydroxy)ethyl, 1-(benzyloxycarbonyloxy)ethyl, 1-(benzoyloxy)ethyl, 1-(phenylacetoxy)ethyl, ethoxy, propoxy, isopropoxy;

R[2] is hydrogen, methyl, ethyl, bromomethyl, hydroxymethyl, methoxymethyl, carbamoyloxymethyl, carboxy, phenoxymethyl, phenyl, acetoxymethyl, aminomethyl, pyridiniomethyl, benzyloxymethyl, 3-pyridyloxymethyl, carboxymethoxymethyl, N-carboxymethylcarbamoyloxymethyl, carboxymethylcarbonyloxymethyl, p-carboxybenzoyloxymethyl, glycyloxymethyl or a CH$_2$—S—Het group wherein Het is a heterocyclic ring preferably chosen from

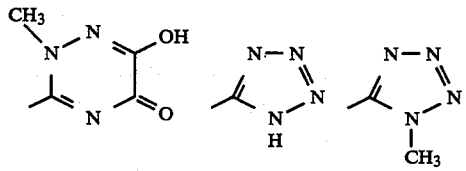

and the pharmaceutically and veterinarily acceptable salts thereof. Possible enolic forms of the above described compounds of general formula (I') are to be considered tautomers of compounds of formula (I') and fall within the scope of the present invention.

It is preferable for A to be as defined under formula (I') above where n is 0, 1 or 2 and m is one or two.

It is preferable for B to be as defined under formula (I') above where n is 0, 1 or 2 and m is one or two.

It is preferable for R' and R'', independently, to be as defined under formula (I') above where n is 0, 1 or 2 and m is one or two.

Specific examples of the preferred compound of the present invention are those listed in Tables I and II.

TABLE I

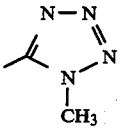

m = 2

| n | R[1] | R[2] | A | B |
|---|------|------|---|---|
| 1 | CH$_3$O | CH$_3$ | t-C$_4$H$_9$ | 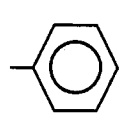 |
| 2 | Cl | CH$_3$ | 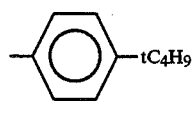 | " |
| 3 | Cl | CH$_3$ | 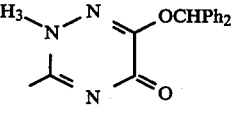—tC$_4$H$_9$ | " |
| 4 | Cl | CH$_3$ | t-C$_4$H$_9$ |  |

TABLE I-continued

[Structure: β-lactam with R⁴ substituent, S(=O)₂ sulfone bridge, =C(R²)-C(=O)-A group, and CH(S-B) side chain; m = 2]

| n | R¹ | R² | A | B |
|---|---|---|---|---|
| 5 | Cl | CH₃ | t-C₄H₉ | 1-methyl-3-methyl-1,2,4-triazin-5(6H)-one-6-carboxylic acid (CH₃-N-N, =N, with COOH, =O) |
| 6 | Cl | CH₃ | –C₆H₅ (phenyl) | " |
| 7 | CH₃O | CH₃ | t-C₄H₉ | 5-methyltetrazol-1-yl-CH₂CH₂CH₂COOH |
| 8 | CH₃O | CH₃ | t-C₄H₉ | 1-methyl-triazinone with OCHPh₂ substituent |
| 9 | CH₃O | CH₃ | t-C₄H₉ | 1-methyl-triazinone-carboxylic acid (as in 5) |
| 10 | Cl | CH₂OCOCH₃ | t-C₄H₉ | 1,5-dimethyltetrazole |
| 11 | CH₃O | CH₃ | cyclopentyl | 1-methyl-triazinone-carboxylic acid |
| 12 | " | " | –CH₂–C(CH₃)₃ (with three CH₃ on central C) | " |
| 13 | " | " | –C(CH₃)₂–C₆H₅ | " |
| 14 | " | " | –CH₂CH₂–C₆H₅ | " |
| 15 | " | " | –CH=CH–CH₃ | " |
| 16 | " | " | –CH₂–C₆H₅ | " |

TABLE I-continued

[Structure shown at top of table with R⁴, sulfonyl group (O=S=O), S—B, R² substituent, N-containing β-lactam ring, C(=O)A group; m = 2]

| n | R¹ | R² | A | B |
|---|----|----|----|----|
| 17 | " | " | —CH(C₆H₅)₂ | " |
| 18 | " | " | cyclohexyl | " |
| 19 | " | " | CH₂OC(=O)C(CH₃)₃ | " |
| 20 | " | " | H | " |
| 21 | " | " | —CH₂CH₃ | " |
| 22 | " | " | $\mathrm{CH_2\text{-}S\text{-}\underset{\underset{CH_3}{|}}{\underset{N}{\text{tetrazole}}}}$ | t-C₄H₉ | " |
| 23 | " | CH₂OCH₃ | " | " |
| 24 | " | H | " | " |
| 25 | " | " | " | 1-methyl-tetrazol-5-yl (with CH₃) |
| 26 | " | " | " | —CH₂COOH |
| 27 | " | CH₃ | " | " |
| 28 | CH₃O | CH₃ | t-C₄H₉ | phenyl |
| 29 | " | " | " | —CH₂CH₂COOH |
| 30 | " | " | " | 5-methyl-1,3,4-thiadiazol-2-yl-CH₂COOH |
| 31 | " | " | " | 5-methyl-1,3,4-thiadiazol-2-yl-SCH₂COOH |
| 32 | " | " | " | 2,5-dimethyl-1,3,4-thiadiazole |

TABLE I-continued
m = 2
| n | R¹ | R² | A | B |
|---|----|----|---|---|
| 33 | " | " | " | 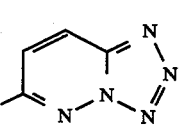 |
| 34 | " | " | " | 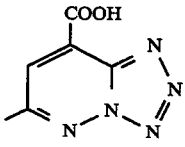 |
| 35 | " | " | " | 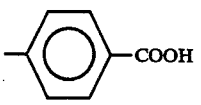 |
| 36 | " | " | " | 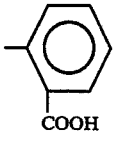 |
| 37 | " | " | " | 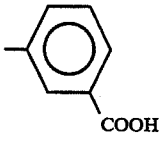 |
| 38 | " | " | " | 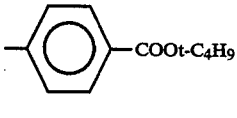 |
| 39 | " | " | " | 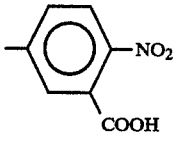 |
| 40 | " | " | " | 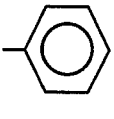 |
| 41 | $CH_3O$ | $CH_3$ | 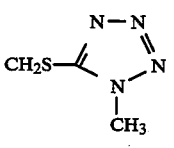 | 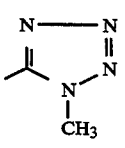 |
| 42 | $CH_3O$ | (tetrazole with $CH_2S$ and $CH_3$) | t-$C_4H_9$ | (tetrazole with $CH_3$) |

TABLE I-continued

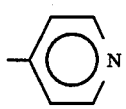

m = 2

| n | R¹ | R² | A | B |
|---|-----|-----|-------|---|
| 43 | CH₃O | CH₃ | t-C₄H₉ | (4-methylpyridyl) |

TABLE II

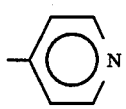

| Entry | R¹ | R² | A | B | m | n |
|-------|------|-----|--------|---|---|---|
| 100 | CH₃O | CH₃ | t-C₄H₉ | (methyl-triazinone-COOH group) | 1 (α-oxide) | 0 |
| 101 | " | " | " | " | 1 (β-oxide) | 0 |
| 102 | " | " | " | (1-methyl-5-methyl-tetrazolyl) | 1 (α-oxide) | 0 |
| 103 | " | " | " | " | 1 (β-oxide) | 0 |
| 104 | Cl | " | " | " | 1 (β-oxide) | " |
| 105 | Cl | " | " | " | 1 (α-oxide) | " |
| 106 | CH₃O | " | " | (phenyl) | 1 (α-oxide) | " |
| 107 | " | " | " | " | 1 (β-oxide) | " |
| 108 | " | " | " | (methyl-triazinone-COOH group) | 1 (α-oxide) | 0 |
| 109 | " | " | " | " | 1 (β-oxide) | 0 |
| 110 | CH₃O | CH₃ | t-C₄H₉ | —CH₃ | 2 | 0 |
| 111 | " | " | " | " | " | 1 |
| 112 | " | " | " | " | " | 2 |
| 113 | " | " | " | —CH₂COOH | " | 1 |
| 114 | " | " | " | " | " | 2 |
| 115 | " | " | " | —CH₂CH₂COOH | " | 1 |
| 116 | " | " | " | " | " | 2 |

TABLE II-continued

| Entry | R¹ | R² | A | B | m | n |
|---|---|---|---|---|---|---|
| 117 | " | " | " | —CH₂—C₆H₄—COOH | " | 1 |
| 118 | " | " | " | " | " | 2 |
| 119 | " | " | " | —CH₂—CH(NHCOCH₃)COOH | " | 0 |
| 120 | " | " | " | " | " | 1 |
| 121 | " | " | " | " | " | 2 |
| 122 | " | " | " | —CH₂COOCH(C₆H₅)₂ | " | 2 |

The compounds of the present invention can be prepared by a process which comprises:

(i) converting a compound of formula (II)

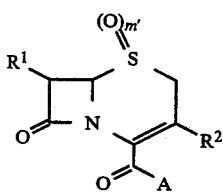     (II)

wherein A, R¹ and R² are as defined above and m' is 0, 1 or 2, into a compound of formula (III)

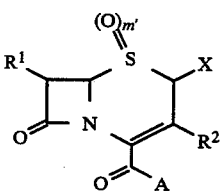     (III)

wherein A, R¹, R² and m' are as defined above and X is halogen;

(ii) reacting the compound of formula (III) with a compound of formula (IV)

$$\overset{(O)_{n'}}{M-S-B}$$ (IV)

wherein n' is 0, 1 or 2 and B is as defined above and M is hydrogen or a metal; and (iii) if desired or needed, converting the resulting compound of formula (I) into another compound of the formula I wherein m and/or n are different from m' and/or n' by oxidation and/or converting a compound of the formula I into a pharmaceutically or veterinarily acceptable salt thereof.

In step (i) the halogen X is preferably chloro, bromo or iodo and in step (ii) the metal is suitably selected from sodium, potassium, lithium, cesium, silver and thallium.

The conversion step (i) is generally carried out by treating compounds of formula (II) with halogenating reagents under conditions which are known in the art to bring about the halogenation of activated hydrogen atoms (see, for example, conditions for the halogenation of aldehydes, ketones, sulphoxides, sulphones described or referred to in "Advanced Organic Chemistry", J. March, McGraw-Hill Ed.).

Suitable halogenating reagents include N-halosuccinimides, halogens and mixed halogens, nitrosylhalides, phenyliodosodihalides, sulphurylhalides, hexahaloethanes, tert-butylipohalides, pyrrolidone hydrotrihalides, cupric halides, phosphorus pentahalides. The halogenation can be carried out in a wide range of organic solvents such as dichloromethane, tetrahydrofuran, dioxane, ethyl acetate, acetonitrile, chloroform, benzene, carbon tetrachloride, methanol, ethanol or acetic acid at a temperature ranging from −60° to +40° C., preferably from −20° C. to room temperature.

The halogenation reaction is usually performed in the presence of a tertiary aliphatic, aromatic or alicyclic organic base such as triethylamine, diisopropylethylamine, aniline, pyridine, lutidine, collidine, quinoline, N-methyl-morpholine, N-methyl-pyrrolidine, N-methylpiperidine, diazabicyclooctane (DABCO); or an inorganic base such as an alkaline bicarbonate or carbonate, for example sodium bicarbonate, calcium carbonate, cesium carbonate, potassium carbonate. If desired, aluminum oxide and silica gel can be employed to catalyse the reaction.

The haloderivative of formula (III) is converted to a compound of formula (I) by treatment with a reagent of formula (IV) in the presence, if necessary, of an organic or inorganic base in a polar aprotic solvent such as acetonitrile, N,N-dimethylformamide, dimethylsulphoxide, N-methylpyrrolidone or hexamethylphosphoramide.

The reaction temperature preferably ranges from $-20°$ to $+40°$ C.

Preferred organic or inorganic bases are as described above.

The compounds of the present invention can alternatively be prepared by a process which comprises reacting a compound of formula (II) as defined above with a reagent of formula (V)

wherein n and B are as defined above and L is a leaving group, in the presence of an organic or inorganic base in an aprotic polar or apolar solvent at a temperature of from $-60°$ to $+40°$ C.

The organic or inorganic base is suitably one of those described above and the temperature is preferably from $-20°$ C. to room temperature.

The leaving group L is preferably a halogen such as chlorine, bromine, or iodine, a $C_1$-$C_3$ alkylsulphonyl such as mesyl or triflyl, an arylsulphonyl such as tosyl, an imido group such as succinimido or phthalimido, or a group

wherein B is as defined above and m is zero, one or two.

Preferred solvents are dichloromethane, chloroform, tetrahydrofuran, acetonitrile, N,N-dimethylformamide, N-methylpyrrolidone, hexamethylphosphoramide, ethyl acetate, dioxane, dimethyleneglycol diethyl ether, 1,2-dichloroethane, dimethoxyethane, benzene and sulpholane. In order to improve the yields and to accelerate the reaction it is possible to add alkaline salts such as sodium iodide or potassium iodide, or heavy metal salts such as silver nitrate, silver perchlorate, silver triflate, copper nitrate or mercury nitrate to the reaction mixture. It is understood that in the process above any functional group, if needed or desired, can be masked by conventional methods and unmasked at the end or when convenient. Also it is understood that a group $R^2$ can be converted by conventional methods into a different group $R^2$ included within those previously defined, if desired, at the end or at any stage of the process above. These conversions or masking/unmasking of the protecting groups are well known on cephalosporins (see, for example, "Cephalosporins and Penicillins", E. H. Flynn Ed.).

The optional oxidation of the compounds of formula I may be carried out with organic or inorganic peracids or their salts, such as peracetic acid, metachloroperbenzoic acid, Oxone (Trade Mark, potassium peroxymonosulfate) or sodium persulphate in suitable organic solvents optionally mixed with water, at a reaction temperature of from $-40°$ to $40°$ C.

Compounds of formula II are described in EP-A-337704 or can be prepared from known compounds therein described by oxidising the sulphur atom at the 1-position of the cephem nucleus to the desired oxidation level ($m'=1$ or 2).

Compounds of formula IV and V are known compounds or can be prepared from known compounds by known methodologies. The potentialities of protease inhibitor therapy in the treatment of conditions resulting from the destruction of connective tissues have recently received particular attention. Much effort has been devoted to the search for inhibitors of human leukocyte elastase (HLE), which is the primary destructive agent in pulmonary emphysema and is probably involved in rheumatoid arthritis (J. C. Power, Am. Rev. Resp. Diseases 127, S54–S58, 1983; C. H. Hassal et al, FEBS Letters, 183, n. 2, 201, 1985, G. Weinbaum and V. V. Damiano, TIPS, 8, 6, 1987; M. Velvart, Rheumatol. Int. 1, 121, 1981). Low molecular weight inhibitors appear to have a number of advantages over natural high molecular weight protease inhibitors from either plant or animal sources: 1) they can be obtained in quantities; 2) they can be rationally designed or optimised; 3) they are not antigenic; and 4) they may be used orally or in aerosols. Many low molecular weight elastase inhibitors discovered so far contain reactive functional groups (chloromethyl ketones, isocyantes, etc); they may react with function groups of proteins, and therefore they may be quite toxic. In this respect, $\beta$-lactam compounds are of potential interest because, though reactive towards serine protease, they are, as it is known, non-toxic at very high concentrations. The compounds of the present invention are characterized by high inhibitory activity on elastases, especially human leukocyte elastase (HLE). In particular, the introduction of the group $-S(O)_n-B$, wherein B and n are as previously described, resulted in an unpredictable enhancement of inhibitory activity, relative to the corresponding $C_2$-unsubstituted compounds (formula II), which are disclosed in EP-A337704.

To illustrate this point, Table 1 reports the results of our preliminary screening test (carried out with porcine pancreatic elastase, PPE), wherein four representative compounds of the present invention (formula I) are compared with the corresponding 2-unsubstitued compounds of formula II (References A and B). This result was completely unexpected, since introduction of the same $C_2$-substituents in cephem sulphones characterized by an ester group at $C_4$ (such as those known in the previous art; see for example Nature 1986, 322, 192) did not improve activity (References C and D).

When tested as inhibitors of human leukocyte elastase (HLE), compounds of formula I showed high "potency" (low apparent dissociation constant of the HLE-inhibitor complex at steady state, $K_i^{ss}$) and high "efficiency" (high rate of formation of the HLE-inhibitor complex, $K_5/K_1$; see Protocol B for the definition of kinetic parameters and conditions for their determination). To illustrate this point, Table 2 reports such parameters for three representative compounds within the present invention, in comparison with Merck S & D L-659,286, another $\beta$-lactam compound reportedly undergoing preclinical studies for the treatment and control of pulmonary emphysema (Am. Rev. Respir. Dis. 1988, 137, 204; Agents and Actions, 1988, 25, 60; Journal of Cellular Biochemistry 1989, 39 47–53). It is interesting to note that compounds of formula (I) do not seem to require the presence of $C_3$ substituents ($R^2$ groups) of the type $-CH_2X$, wherein X is an electron-withdrawing group, or a leaving group, such as acetoxy. Till know, this type of substitution was considered to play a major role in the inhibition mechanism of cephem sulphones (Nature 1987, 327, 79). Surprisingly, in compounds of formula I such type of activation was found to be dispensable. Thus, for example, the group of compounds of formula I wherein $R^2$ is methyl, as exemplified in table II above, are highly active, while retaining good levels of chemical stability, characteristic of this particular substitution at $C_3$.

TABLE 1

PPE-inhibitory activity[1] of four representative compounds of formula I, characterizing the present invention, in comparison with the corresponding compounds of formula II and related structures

| Compound | $IC_{50}$ ($\mu$g/ml) |
| --- | --- |
| n° 4 (Example 10) | 0.045 |
| n° 5 (Example 11) | 0.035 |
| n° 9 (Example 4) | 0.030 |
| n° 1 (Example 2) | 0.040 |
| References[2] of formula II: | |
| Reference A | 2.0 |
| Reference B | 2.0 |
| Cephem 4-carboxylate references[2]: | |
| Reference C | 2.0 |
| Reference D | 5 |

[1] See Protocol A for conditions
[2] Structure of reference compounds:

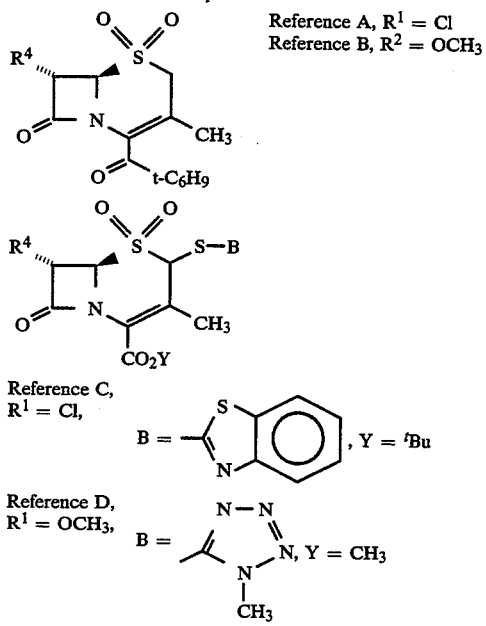

Reference A, $R^1$ = Cl
Reference B, $R^2$ = $OCH_3$

Reference C, $R^1$ = Cl, B = benzothiazol-2-yl, Y = $^tBu$

Reference D, $R^1$ = $OCH_3$, B = (methyl-triazolyl), Y = $CH_3$

TABLE 2

Kinetic parameters for HLE-inhibition[2] by three representative compounds of formula I, in comparison with related $\beta$-lactam compounds

| Compound | "Potency" $K_i$ (nM) | "Efficacy" $K_{on}$ ($10^4 M^{-1}S^{-1}$) |
| --- | --- | --- |
| n° 1 (Example 2) | 8.3 | 9 |
| n° 7 (Example 8) | 18 | 1.1 |
| n° 9 (Example 4) | 26 | 2.5 |
| Reference compounds: | | |
| Merck L-659,286[2] | 140 | 0.15 |
| Reference D[3] | 38.000 | 0.05 |

[1] See Protocol B for definition and conditions
[2] Structure:

TABLE 2-continued

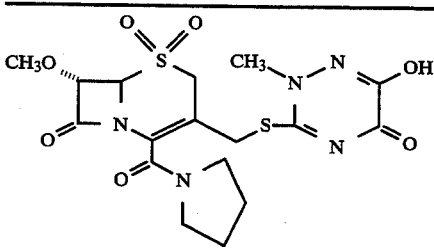

This compound was synthesized in our laboratories from 7-amino-3-desacetoxycephalosporanic acid. Its structural identity and purity ($\geq$95%) was confirmed by spectral and analytical data
[3] See Table 1, note 2 for structure.

Protocol A—Inhibition of PPE activity was determined at 30° C., 0.05M pH 7.4 phosphate buffer, 2.5% MeCN, by monitoring the release of p-nitroaniline (410 nm, Carlo Erba Strumentazione Spectracomp spectrophotometer) from the substrate (N-t-Boc-alanyl-alanyl-prolyl-alanine-p-nitroanilide, 0.2 mM initial concentration). Results indicate the inhibitor concentration effective for 50% reduction of the enzyme activity 6.4 minutes after zero time.

Protocol B—Inhibition of HLE activity (Calbiochem, Lot 702038) was determined at 37° C., 0.027M pH 7.4 phosphate buffer, 1% DMSO, 1% MeCN, NaCl (I=15), by monitoring the release of 7-amino-4-methylcoumarin (fluorescence detection) from N-methoxysuccinyl-alanyl-prolyl-valyl-7-amido-4-methylcoumarin as substrate, according to the equations:

$$[P] = v_s t + \frac{(v_s - v_z)}{k}(1 - e^{-kt}) + S = ES - E +$$

$$Pk = k_{off} + \frac{k_{on}[I]}{1 + [S]/k_m} E +$$

$$I \frac{k_{on}}{k_{off}} V_s = V_o \frac{1 + [S]/k_m}{1 + [S]/k_m + [I]/k_i}$$

$k_i = k_{off}/k_{on}, V_s = V_o$ wherein:
[P], [I], [S]=product, inhibitor and substrate concentration
$v_s$=steady state rate
$v_z$=zero time rate
$v_o$=rate at [I]=O
$k_m$=Michaelis constant for the enzyme-substrate pair (independently determined under the same experimental conditions).

Owing to their high elastase-inhibiting activity and their quite negligible toxicity, (the orientative acute toxicity is almost always greater than 500 mg/Kg in rat) the compounds of the present invention can be used in the treatment of inflammatory and degenerative diseases caused by proteolytic enzymes in mammals including humans. The compounds can be used to make medicaments useful to prevent or arrest the progression of diseases caused by proteolytic degradation of lungs and connective tissues, reduce inflammation and fever, and relieve pain. Such diseases are emphysema, acute respiratory distress syndrome, bronchial inflammation, rheumatoid arthritis, osteoarthritis, infectious arthritis, rheumatic fever, spondylitis, gout, lupus, psoriasis, and the like.

Accordingly, the present invention also provides pharmaceutical and veterinary compositions containing a suitable carrier and/or diluent and, as an active principle, a 4-acylcephem sulphone of formula (I) or a pharmaceutically or veterinarily acceptable salt thereof.

The pharmaceutical or veterinary compositions containing a compound of formula (I) or salt thereof may be prepared in a conventional way by employing conventional non-toxic pharmaceutical carriers or diluents in a variety of dosage forms and ways of administration. In particular, the compounds of formula (I) can be administered:

a) orally, for example, as tablets, troches, lozenges, aqueous or oily suspensions, dispersible powders or granules, emulsions, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets.

These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelating or acacia, and lubricating agents, for example magnesium stearate, stearic acid or talc.

The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed.

Formulation for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl or n-propyl p-hydroxybenzoate, one or more coloring agents, one or more flavoring agents, or one or more sweetening agents, such as sucrose or saccharin. Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives.

Suitable dispersing or wetting agents and suspending agents are exemplified by those already mentioned above. Additional excipients, for example sweetening, flavouring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsion may also contain sweetening and flavoring agents. Syrups and elixirs may be formulated with sweetening agents, for example glycerol, sorbitol or sucrose. Such formulations may also contain a demulcent, a preservative and flavoring and coloring agents.

b) parenterally, either subcutaneously, or intravenously, or intramuscularly, or intrasternally, or by infusion techniques, in the form of sterile injectable aqueous or oleagenous suspensions. The pharmaceutical compositions may be in the form of a sterile injectable aqueous or olagenous suspension.

This suspension may be formulated according to the known art using those suitable dispersing of wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium.

For this purpose any bland fixed oil may be employed including synthetic mono- or diglycerides. In addition fatty acids such as oleic acid find use in the preparation of injectables;

c) by inhalation, in the form of aerosols or solutions for nebulizers;

d) rectally, in the form of suppositories prepared by mixing the drug with a suitable non-irritating excipient which is solid at ordinary temperature but liquid at the rectal temperature and will therefore melt in the rectum to release the drug. Such materials are cocoa butter and polyethylene glycols;

e) topically, in the form of creams ointments, jellies, solutions or suspensions.

Still a further object of the present invention is to provide a method of controlling inflammatory and degenerative diseases by administering a therapeutically effective amount of one or more of the active compounds encompassed by the formula (I) in humans or mammalians in need of such treatment.

Daily dose are in the range of about 0.5 to about 100 mg per kg of body weight, according to the activity of the specific compound, the age, weight and conditions of the subject to be treated, the type and severity of the disease, and the frequency and route of administration; preferably, daily dosage levels for humans are in the range of 50 mg to 2 g. The amount of active ingredient that may be combined with the carrier materials to produce a single dosage form will vary depending upon the host treated and the particular mode of administration.

For example, a formulation intended for the oral administration to humans, may contain from 5 mg to 2 g of active agent compounded with an appropriate and convenient amount of carrier material which may vary from about 5 to about 95 percent of the total composition. Dosage unit forms will generally contain between from about 25 mg to about 500 mg of active ingredient.

EXAMPLE 1

2-Bromo-4-tert-butylcarbonyl-7α-methoxy-3-methyl-3-cephem, 1,1-dioxide

A solution of 4-tert-butylcarbonyl-7α-methoxy-3-methyl-3-cephem, 1,1-dioxide (300 mg), in dichloromethane (20 ml), was treated, at room temperature, with triethylamine (0.015 ml) and NBS (178 mg).

After 30 min. more NBS (178 mg) was added.

After additional 30 min. the solvent was removed in vacuo and the residue purified by flash chromatography, thereby obtaining the title compound as a white powder (180 mg).

Mp 144°–145° C.

NMR (200 MHz, CDCl$_3$) δ1.29 (9H,s), 1.82 (3H,s), 3.57 (3H,s), 4.89 (1H,s), 5.16 (1H,d,J=1.9 Hz), 5.31 (1H,d,J=1.9 Hz) ppm.

EXAMPLE 2

4-tert-Butylcarbonyl-7α-methoxy-3-methyl-2-(1-methyl-1,2,3,4-tetrazol-5-yl)thio-3-cephem 1,1-dioxide (Compound 1)

A solution of 2-Bromo-4-tert-butylcarbonyl-7α-methoxy-3-methyl-3-cephem, 1,1-dioxide (95 mg) (prepared as described in Example 1) in dimethylformamide (2 ml), was treated with sodium 1-methyl-1,2,3,4-tetrazolyl-5-mercaptide (66 mg).

After 10 min. the reaction mixture was diluted with dichloromethane and washed with brine. Removal of the solvent and flash chromatography afforded the title compound as a yellowish solid (55 mg).

Mp 74°–7° C.

IR (KBr) νmax 1795, 1700 cm$^{-1}$.

NMR (200 MHz, CDCl$_3$) δ1.29(9H,s), 1.92(3H,s), 3.56(3H,s), 4.09(3H,s), 4.99(1H,s), 5.12(1H,d,J=1,9 Hz), 5.18(1H,d,J=1.9 Hz) ppm.

EXAMPLE 3

4-tert-Butylcarbonyl-7α-methoxy-3-methyl-2-(2-methyl-5-oxo-6-benzhydryloxy-2,5-dihydro-1,2,4-triazin-3-yl)thio-3-cephem 1,1-dioxide (Compound 8)

A solution of 2-bromo-4-tert-butylcarbonyl-7α-methoxy-3-methyl-3-cephem 1,1-dioxide (180 mg), prepared as in Example 1, in dry acetonitrile (30 ml) was treated with triethylamine (0.07 ml) and 3-mercapto-2-methyl-5-oxo-6-benzhydryloxy-2,5-dihydro-1,2,4-triazine (168 mg).

After 30 min. the reaction mixture was diluted with ethylacetate and washed with brine.

Removal of the solvent in vacuo and flash chromatography afforded the title compound (170 mg) as a yellowish powder.

IR (CHCl$_3$) νmax 1795, 1675 (broad) cm$^{-1}$.

NMR (200 MHz, CDCl$_3$) δ1.27 (9H,s), 1.79 (3H,s), 3.55 (3H,s), 3.69 (3H,s), 5.04 (1H,d,J=1.8 Hz), 5.10 (1H,d,J=1.8 Hz), 5.83 (1H,s) 6.71 (1H,s), 7.08–7.46 (10H,m) ppm.

EXAMPLE 4

4-tert-Butylcarbonyl-7α-methoxy-3-methyl-2-(2-methyl-5-oxo-6-hydroxy-2,5-dihydro-1,2,4-triazin-3-yl)thio-3-cephem 1,1-dioxide (Compound 9)

179 mg of 4-tert-butylcarbonyl-7α-methoxy-3-methyl-2-(2-methyl-5-oxo-6-benzhydryloxy-2,5-dihydro-1,2,4-triazin-3-yl)thio-3-cephem 1,1-dioxide, prepared following the experimental procedure described in Example 3, was dissolved in dichloromethane (2 ml) and anisole (0.018 ml) and trifluoroacetic acid (1 ml) were added. After 15 min, TFA was completey removed in vacuo and the residue taken up in dichloromethane (1 ml). Addition of isopropyl ether afforded the title compound (125 mg) as a white powder.

mp 122°–5° C.

IR (KBr) νmax 1790, 1700, 1650 (broad) cm$^{-1}$.

NMR (200 MHz, CDCl$_3$) δ1.28 (9H,s), 1.84 (3H,s), 3.56 (3H,s), 3.82 (3H,s), 4.98 (1H,d,J=1.2 Hz), 5.19 (1H,d,J=1.2 Hz), 5.91 (1H,s) ppm.

EXAMPLE 5

4-Phenylcarbonyl-7α-chloro-3-methyl-2-(1-methyl-1,2,3,4-tetrazol-5-yl)thio-3-cephem 1,1-dioxide (Compound 2)

A solution of 2-bromo-7α-chloro-3-methyl-4-phenylcarbonyl-3-cephem 1.1-dioxide (82 mg) prepared starting from 4-phenylcarbonyl-7α-chloro-3-methyl 1,1-dioxide and following the experimental procedure described in Example 1, in dimethylformamide (1 ml) was treated with sodium 1-methyl-1,2,3,4-tetrazolyl-5-mercaptide (60 mg). An immediate reaction took place (TLC monitoring). Dilution with dichloromethane, washing with brine, drying over Na$_2$SO$_4$ and removal of the solvent left a residue which afforded the title compound as a yellowish solid after flash chromatography.

mp 68°–70° C.

IR (CHCl$_3$) νmax 1810, 1675 cm$^{-1}$.

NMR (200 MHz, CDCl$_3$) δ1.92 (3H,s), 4.11 (3H,s), 5.28 (1H,s), 5.32 (1H,d,J=2.0 Hz), 5.37 (1H,d,J=2.0 Hz), 7.51–8.02 (5H,m) ppm.

EXAMPLE 6

4-(4-tert-Butylphenyl)carbonyl-7α-chloro-3-methyl-2-(1-methyl-1,2,3,4-tetrazol-5-yl)thio-3-cephem 1,1-dioxide (Compound 3)

A solution of 2-bromo-4-(4-tert-butylphenyl)carbonyl-7α-chloro-3-methyl-3-cephem 1,1-dioxide (80 mg) prepared starting from 4-(4-tert-butylphenyl)carbonyl-7α-chloro-3-methyl-3-cephem 1.1-dioxide (125 mg) and following the experimental procedure described in Example 1, in dimethylformamide (2 ml) was treated with sodium 1-methyl-1,2,3,4-tetrazolyl-5-mercaptide (57 mg).

After 10 min. the reaction mixture was diluted with dichloro methane and washed with brine. Drying over $Na_2SO_4$ and removal after solvent left a residue which was then purified by flash chromatography affording the title compound as a yellowish solid (33 mg).

m.p. 112°–115° C.

IR ($CHCl_3$) $\nu$max 1810, 1675 cm$^{-1}$.

NMR (200 MHz, $CDCl_3$) $\delta$1.36 (9H,s), 1.92 (3H,s), 4.10 (3H,s), 5.29 (1H,s), 5.33 (1H,d,J=2.0 Hz), 5.37 (1H,d,J=2.0 Hz), 7.71 (4H,AB$_q$,J=8.6) ppm.

EXAMPLE 7

3-Acetoxymethyl-4-tert-butylcarbonyl-7α-chloro-2-(1-methyl-1,2,3,4-tetrazol-5-yl)thio-3-cephem 1,1-dioxide (Compound 10)

A solution of 3-acetoxymethyl-2-bromo-4-tert-butylcarbonyl-7α-chloro-3-cephem 1,1-dioxide (60 mg) prepared starting from 3-acetoxymethyl-4-tert-butylcarbonyl-7α-chloro-3-cephem 1,1-dioxide and following the experimental procedure described in Example 1, in dimethylformamide (1 ml) was treated, at room temperature, with sodium 1-methyl-1,2,3,4-tetrazolyl-5-mercaptide (36 mg).

An immediate reaction took place. Dilution with dichloromethane, washing with brine, drying over $Me_2SO_4$ and removal of the solvent in vacuo left the residue which, purified by flash chromatography, afforded the title compound as a light yellow solid (20 mg).

mp 65°–8° C.

IR ($CHCl_3$) $\nu$max 1810, 1730, 1695 cm$^{-1}$.

NMR (200 MHz, $CDCl_3$) $\delta$1.30 (9H,s), 2.14 (3H,s), 4.08 (3H,s), 4.31 and 4.77 (2H, each d, J=13.3 Hz), 5.30 (1H,d, J=2.0), 5.40 (1H,d,J=2.0 Hz) 5.41 (1H,s) ppm.

EXAMPLE 8

4-tert-Butylcarbonyl-7α-methoxy-3-methyl-2-[1-(3-carboxy-1-propyl)-1,2,3,4-tetrazol-5-yl]thio-3-cephem 1,1-dioxide (Compound 7)

A solution of 2-bromo-4-tert-butylcarbonyl-7α-methoxy-3-methyl-3-cephem 1,1-dioxide (95 mg), prepared as described in Example 1, in dry acetonitrile (15 ml) was treated with triethylamine (0.06 ml) and 5-mercapto-[1-(3-carboxy-1-propyl)-1,2,3,4-tetrazole (60 mg).

After 20 min. the reaction mixture was diluted with ethylacetate and the product extracted with aq. NaHCO$_3$. Addition of HCl (37%), back-extraction with ethyl acetate, washing with brine, drying over $Na_2SO_4$ and removal of the solvent, left the crude title product, which was then obtained pure (82 mg) as a yellowish solid, after flash chromatography.

m.p. 70°–3° C.

IR (KBr) $\nu$max 1800, 1700 (broad) cm$^{-1}$.

NMR (200 MHz, $CDCl_3$) $\delta$1.29 (9H,s), 1.93 (3H,s), 2.31 (2H,m), 2.49 (2H,m), 4.53 (2H,m), 5.16(1H,s), 5.18(1H,d, J=2.0 Hz), 5.24 (1H,d, J=2.0 MHz) ppm.

EXAMPLE 9

4-tert-Butylcarbonyl-7α-methoxy-3-methyl-2-(5-methyl-1,3,4-thiadiazol-2-yl)thio-3-cephem 1,1-dioxide (Compound 32)

A solution of 2-bromo-4-tert-butylcarbonyl-7α-methoxy-3-methyl-3-cephem 1,1-dioxide (40 mg), prepared as in Example 1, in dry acetonitrile (10 ml) was treated with triethylamine (0.02 ml) and 2-mercapto-5-methyl-1,3,4-thiadiazole (28 mg).

After 15 min. the reaction mixture was diluted with dichloromethane and washed with brine. Drying over $Na_2SO_4$ and removal of the solvent left a residue which, purified by flash chromatography, afforded the title compound as a light yellow solid (25 mg).

m.p. 116°–7° C.

IR ($CHCl_3$) $\nu$max 1790, 1700 cm$^{-1}$.

NMR (200 MHz, $CDCl_3$) $\delta$1.21 (9H,s), 1.9 (3H,s), 2.8 (3H,s), 3.5 (3H,s), 5.19 (1H,d,J=2.0 Hz), 5.21 (1H,s), 5.26 (1H,d,J=2.0 Hz) ppm.

EXAMPLE 10

4-Tert-butylcarbonyl-7α-chloro-3-methyl-2-(2-methyl-5-oxo-6-benzhydryloxy-2,5-dihydro 1,2,4-triazin-3-yl-)thio-3-cephem 1,1-dioxide (compound 4)

A solution of 2-bromo-4-tert-butylcarbonyl-7α-chloro-3-methyl-3-cephem-1,1-dioxide (192 mg), prepared starting from 4-tert-butylcarbonyl-7α-chloro-3-methyl-3-cephem 1,1-dioxide and following the experimental procedure described in example 1, in dry acetonitrile (30 ml) was treated with triethylamine (0.07 ml) and 3-mercapto-2-methyl-5-oxo-6-benzhydryloxy-2,5-dihydro-1,2,4-thiazine (170 mg). After 30 min. the reaction mixture was diluted with ethylacetate and washed with brine. Removal of the solvent in vacuo and flash chromatography afforded the title compound. (160 mg) as a yellowish powder.

IR($CHCl_3$) $\nu$max 1795, 1690, 1670 cm$^{-1}$.

EXAMPLE 11

4-tert-butylcarbonyl-7α-chloro-3-methyl-2-(2-methyl-5-oxo-6-hydroxy-2,3-dihydro-1,2,4-triazin-3-yl)-thio-3-cephem 1,1-dioxide (compound 5)

Starting from 4-tert-butylcarbonyl-7α-chloro-3-methyl-2-(2-methyl-5-oxo-6-benzhydryloxy-2,5-dihydro-1,2,4-triazin-3-yl)-thio-3-cephem 1,1-dioxide (160 mg) and following the experimental procedure described in example 4, the title compound was obtained pure as a yellowish powder (95 mg)

IR($CHCl_3$) $\nu$max 1790, 1700, 1650 (large) cm$^{-1}$.

EXAMPLE 12

7α-Methoxy-3-methyl-2-(1-methyl-1,2,3,4-tetrazol-5-yl)thio-4-phenylcarbonyl-3-cephem 1,1-dioxide (compound 41)

Starting from 7α-methoxy-3-methyl-4-phenylcarbonyl-3-cephem 1,1-dioxide and following the experimental procedure described in Example 1, 2-bromo-7α-methoxy-3-methyl-4-phenylcarbonyl-3-cephem 1,1-dioxide was prepared. A solution of this compound (80 mg) in dry acetonitrile (15 ml) was treated with sodium 1-methyl-1,2,3,4-tetrazolyl-5-mercaptide dihydrate (66 mg). An immediate reaction took place. Dilution with dichloromethane, washing with brine, drying over $Na_2SO_4$ and removal of the solvent left a residue, which afforded the title compound (75 mg) as a yellowish solid after flash chromatography;

m.p. 113°–115° C.

IR (KBr) $\nu_{max}$ 1800, 1680 cm$^{-1}$.

NMR (200 MHz, $CDCl_3$) $\delta$1.90 (3H,s), 3.51 (3H,s), 4.08(3H,s), 5.19(1H,s), 5.20(2H,s), 7.48–7.91(5H,m) ppm.

EXAMPLE 13

4-Tert-butylcarbonyl-7α-methoxy-2-(1-methyl-1,2,3,4-tetrazol-5-yl)thio-3-(1-methyl-1,2,3,4-tetrazol-5-yl)thiomethyl-3-cephem 1,1-dioxide (compound 42)

Step A: A solution of 4-tert-butylcarbonyl-7α-methoxy-3-methyl-3-cephem 1,1-dioxide (300 mg) in carbon tetrachloride was refluxed in the presence of NBS (300 mg) and azo-bis-isobutyronitrile (10 mg). After 4 h, removal of the solvent and chromatography afforded 2-bromo-3-bromomethyl-4-tert-butylcarbonyl-7α-methoxy-3-cephem 1,1-dioxide (120 mg) as a white powder;

IR (KBr) $\nu_{max}$ 1800, 1690 cm$^{-1}$;

NMR (200 MHz, CDCl$_3$) δ1.26 (9H,s), 3.58(3H,s), 3.77 and 4.03 (2H, each d, J=11.2 Hz), 5.19(1H,d, J=2.2 Hz), 5.36(1H,d, J=2.2 Hz), 5.46 (1H,s) ppm.

Step B: A solution of the compound from step A above (120 mg) in dry acetonitrile (20 ml) was treated with sodium 1-methyl-1,2,3,4-tetrazolyl-5-mercaptide dihydrate (70 mg). After 15 min, the reaction mixture was diluted with dichloromethane and washed with brine. Removal of the solvent left a residue which was purified by flash chromatography over SiO$_2$ (ethyl acetate-hexane as eluant) affording the title compound as a yellowish solid (125 mg);

m.p. 97°–100° C.;

IR (KBr) $\nu_{max}$ 1800, 1700 cm$^{-1}$;

NMR (200 MHz, CDCl$_3$) δ1.27 (9H,s), 3.53(3H,s), 3.68 and 4.34 (2H, each d, J=14.3 Hz), 4.11(3H,s), 5.01(1H,d,J=1.9 Hz), 5.21(1H,d,J=1.9 Hz), 5.55(1H,s).

EXAMPLE 14

4-Tert-butyl-7α-methoxy-3-methyl-2-(2-pyridyl)thio-3-cephem 1,1-dioxide (compound 33)

A solution of 4-tertbutyl-7α-methoxy-3-methyl-3-cephem 1,1-dioxide (100 mg) in dry acetonitrile (4 ml) was sequentially treated with bis-(2-pyridyl)disulphide (160 mg) and diazobicyclononane (DBN) (50 ml). The resulting mixture was stirred for 30 minutes at r.t. then poured into EtOAc/2% aq.HCl:

Following drying over Na$_2$SO$_4$ the organic phase was concentrated in vacuo. The residue was chromatographed over silica gel (ethyl acetate/cyclohexane mixture as eluants). The title product was obtained as a white foam (62 mg);

IR (KBr) $\nu_{max}$ 1798, 1696 cm$^{-1}$.

NMR (200 MHz), CDCl$_3$) 1.27 (9H,s); 1.87 (3H, s); 3.54 (3H, s); 5.04 (1H,d, J=1.8 Hz); 5.16 (1H, d, J=1.8 Hz); 6.10 (1H,s); 7.1–7.3 (1H, m); 7.5–7.7 (1H, m); 8.5 (1H, m).

EXAMPLE 15

4-Tert-butyl-7α-methoxy-3-methyl-2-methylthio-3-cephem 1,1-dioxide (compound 110)

Following a similar procedure to that described in Example 14 and substituting methyl methanethiosulphonate for bis(2-pyridyl)disulphide the title product was obtained as a white powder IR (KBr) $\nu_{max}$ 1795, 1700 cm$^{-1}$.

EXAMPLE 16

4-Tert-butyl-7α-methoxy-3-methyl-2-(benzhydryloxycarbonylmethyl)thio-3-cephem 1,1-dioxide (compound 122)

Following a similar procedure to that described in example 14 and substituting bis(benzhydryloxycarbonylmethyl)disulphide for bis(2-pyridyl)disulphide the title product was obtained as a white foam.

IR(CHCl$_3$) 1795, 1730–1690 cm$^{-1}$.

EXAMPLE 17

4-Tert-butyl-7α-methoxy-3-methyl-2-methyl-sulphinyl-3-cephem 1,1-dioxide (compound 111) and
4-Tert-butyl-7α-methoxy-3-methyl-2-methylsulphonyl-3-cephem 1,1-dioxide (compound 112)

A solution of 4-tert-butyl-7α-methoxy-3-methyl-2-methylthio-3-cephem 1,1-dioxide (40 mg) in dichloromethane (4 ml) at −20° C. was treated with 55% m-chloroperbenzoic acid (70 mg). Stirring was continued for 4 h at room temperature. Following work-up with aqueous NaHSO$_3$ and aqueous NaHCO$_3$. The organic phase was concentrated and the residue was chromatographed over silica gel allowing the isolation of the title products (respectively the slower and faste running in ethyl acetate/cyclohexane 2:1).

sulphoxide (compound 111), MS (FD) 363 m/z.
sulphone (compound 112), MS (FD) 379 m/z.

EXAMPLE 18

4-Tert-butyl-7α-methoxy-3-methyl-2-(carboxymethyl)thio-3-cephem 1,1-dioxide (compound 26)

To a solution of 4-tert-butyl-7α-methoxy-3-methyl-2-(benzhydryloxycarbonylmethyl)thio-3-cephem 1,1-dioxide (see Example 16) (20 mg) in dichloromethane (0.5 ml), anisole (60 ml) and trifluoroacetic acid (0.3 ml) were added sequentially. The mixture was let stand for 3 hours at room temperature then concentrated in vacuo. Diisopropylether (10 ml) was added under stirring. The light yellow powder thus obtained was filtered and dried in vacuo (12 mg).

EXAMPLE 19

4-Tert-butyl-7α-methoxy-3-methyl-2-(carboxymethyl)-sulphinyl-3-cephem 1,1-dioxide sodium salt (compound 113)

A solution of 4-tert-butyl-7α-methoxy-3-methyl-2-(carboxymethyl)thio-3-cephem 1,1-dioxide (25 mg) in dichloromethane (2 ml) at −10° C. was treated with 80% m-chloroperbenzoic acid (13 mg). After stirring 10 minutes at −10° C., dimethylsulphide (10μ) was added and the mixture was warmed to room temperature. Solvent was removed in vacuo. The residue was taken up with water (0.5 ml) and the pH was adjusted to 7 with the slow addition of 1% aq. NaHCO$_3$.

The resulting solution was passed through a reversed phase column (LiChroprep C-18) eluting with water. Then water/acetonitrile mixtures. The product containing fractions were freeze-dried affording the title compound as a white powder (16 mg).

EXAMPLE 20

4-Tert-butylcarbonyl-7α-methoxy-3-methyl-2-(2-methyl-5-oxo-6-hydroxy-2,5-dihydro-1,2,4-triazin-3-yl)thio-3-cephem 1α-oxide (compound 100)

A solution of 4-tert-butylcarbonyl-7α-methoxy-3-methyl-3-cephem 1α-oxide (570 mg) in dichloromethane (40 ml) and carbon tetrachloride (60 ml) was treated with N-bromosuccinimide (420 mg) and 2,2′-azo-bis (2-methylpropionitrile) (20 mg) and heated at reflux for 5 hours. Removal of the solvent and silica gel chromatography of the residue allowed the isolation of 4-tertbutylcarbonyl-7α-methoxy-2-bromo-3-methyl-3-cephem-1α-oxide (190 mg; faster running product) and 4-tert-butylcarbonyl-7α-methoxy-3-bromomethyl-3-cephem α-oxide (180 mg; slower running product).

The 2-bromo derivative was dissolved in dry acetonitrile (20 ml) and sequentially treated with 3-mercapto-2-methyl-5-oxobenzhydryloxy-2,5-dihydro-1,2,4-triazine (315 mg) and triethylamine (140 ml). After stirring for 4 hours at room temperature the reaction mixture was poured into ethylacetate/water. The organic phase was dried over $Na_2SO_4$ and evaporated. Chromatography of the residue allowed the isolation of the benzhydryl derivative of the title product, which was treated with dichloromethane: trifluoacetic acid: anisole 10:5:0.5 (10 ml) for 1 hour at room temperature. The solvent was removed under vaccum. The residue was taken-up with a small amount of $CH_2Cl_2$ and diisopropylether was added under stirring. The precipitate was filtered and washed with diethylether. The title product was thus obtained as a white powder (160 mg), m.p. 156°–158° C.

IR(KBr) $\nu_{max}$ 1780, 1690, 1650 cm$^{-1}$.

NMR (CDCl$_3$, 200 MHz) δ1.23 (9H, s), 1.87 (3H, s), 3.55 (3H, s), 3.88 (3H, s), 4.35 (1H, d, J=1.9 Hz) 5.01 (1H, d, J=1.9 Hz) 6.38 (1H, s).

EXAMPLE 21

4-Tert-butylcarbonyl-7α-methoxy-3-methyl-2-(2-methyl-5-oxo-6-hydroxy-2,5-dihydro-1,2,4-triazin-3-yl)thio-3-cephem 1β-oxide (compound 101)

Starting from 4-tert-butylcarbonyl-7α-methoxy-3-methyl-3-cephem 1β-oxide and following the procedure described in example 20, the title product was obtained as a white powder.

IR(KBr) $\nu_{max}$ 1785, 1703, 1765 cm$^{-1}$

NMR (CDCl$_3$, 200 MHz) δ1.28 (9H, s), 1.86 (3H, s), 3.58 (3H, s), 3.73 (3H, s), 4.62 (1H, s), 4.99 (1H, s), 5.77 (1H, s).

EXAMPLE 22

4-Tert-butylcarbonyl-7α-methoxy-3-methyl-2-(1-methyl-1,2,-3,4-tetrazol-5-yl)thio-3-cephem 1α(compound 102)

4-tert-butylcarbonyl-7α-methoxy-3-methyl-2-bromo-3-cephem 1α-oxide (30 mg), prepared as described in example 20, was dissolved in acetonitrile (2 ml) and treated with sodium 1-methyl-1,2,3,4-tetrazolyl-5-mercaptide (20 mg). After stirring 2 hours at room temperature the mixture was partitioned between ethyl acetate and water. The organic phase, following drying over $Na_2SO_4$, was concentrated, leaving a residue which afforded the title product as a white solid after flash chromathopgraphy m.p. 160°–165° C.

NMR (CDCl$_3$, 200 MHz) δ1.25 (9H, s), 2.02 (3H, s), 3.56 (3H, s), 4.10 (3H, s), 4.49 (1H, d, J=1.9 Hz), 5.02 (1H, d, J=1.9 Hz), 5.58 (1H, s).

We claim:

1. A compound of the formula (I')

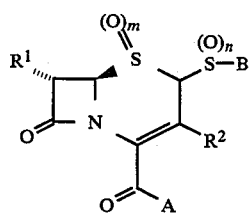

wherein n is zero, one or two; m is one or two;

A is methyl or $C_2$–$C_{10}$ straight or branched alkyl, alkenyl, alkynyl; $C_3$–$C_8$ cycloalkyl; dimethylphenyl, diphenylmethyl; phenyl or benzyl; wherein the alkyl, alkenyl, alkynyl, cycloalkyl, phenyl and benzyl groups are either unsubstituted or substituted by fluoro, chloro, carboxy, $C_1$–$C_4$ alkoxycarbonyl, carbamoyl, carbamoyloxy, methylsulphonyl, diazo, hydroxy, methoxy, ethoxy, tertbutoxy, benzyloxy, acetoxy, pivaloyloxy, benzoxy or phenylacetoxy;

B is
- (1') optionally substituted $C_1$–$C_5$ straight or branched alkyl or alkenyl or $C_1$–$C_5$ cycloalkyl;
- (2') optionally substituted phenyl;
- (3') optionally substituted aralkyl; or
- (4') an optionally substituted 5- or 6-membered saturated or unsaturated heterocyclic ring, containing one or more heteroatoms selected from O, S, N, optionally fused to a second said 5- or 6-membered carbocyclic or heterocyclic ring, the substituents for the groups defined under (1')–(4') being selected from hydroxy, $C_1$–$C_3$ alkoxy, phenoxy, benzyloxy, benzhydryloxy, methylthio, carboxy, carboxymethyl, carboxyethyl, carbamoylmethyl, amino, acetamido, formamido, dimethylamino, diethylamino, dimethylaminoethyl, nitro, cyano, sulpho, sulphamoyl, tetrazolyl, formimidoyl, ureido, chloro, fluoro, bromo, oxo, $C_1$–$C_5$ alkyl, vinyl and allyl;

$R^1$ is hydrogen or
- (1') chloro, fluoro or bromo;
- (2') $C_1$–$C_4$ alkyl, 1-(hydroxyl)ethyl, 1-(benzyloxy)-ethyl, 1-(benzyloxycarbonyloxy)ethyl, 1-(phenylacetoxy)ethyl, isopropyl phenyl, benzyl or allyl;
- (3') methoxy, ethoxy, isopropoxy, phenoxy or benzyloxy;
- (4') methylthio;
- (5') formyloxy, acetoxy or phenylacetoxy;
- (6') mesyloxy or tosyloxy;
- (7') formamido, acetamido, fluoroacetamido, trifluoroacetamido or chloroacetamido;
- (8') $R^v$-Ala-NH, wherein $R^v$ is either acetyl, tert-butoxycarbonyl, benzoxycarbonyl or HOO-C—$CH_2CH_2$C(O)—;
- (9') $R^v$-Val-NH wherein $R^v$ is as defined above;
- (10') Val-Pro-NH, Lys-NH or Ala-Ala-Pro-NH, wherein the terminal amino group of Val, Lys or Ala respectively or the α-amino group of Lys is either free or acylated with a group $R^v$ as defined above;

$R^2$ is either hydrogen or
- (1') methyl, chloromethyl, bromomethyl, benzyl, ethyl, propyl or phenyl;
- (2') chloro;
- (3') methoxy or benzyloxy;

(4') methylthio;

(5') formyl, acetyl, benzoyl, carboxy, methoxycarbonyl, ethoxycarbonyl, tert-butoxycarbonyl or benzyloxycarbonyl;

(6') methoxymethyl, ethoxymethyl, isopropoxymethyl, benzyloxymethyl, phenoxymethyl or 3-pyridyloxy-methyl, wherein the phenyl and pyridyl rings are either unsubstituted or substituted by one group or two groups which are the same or different, the said group or groups being chosen from hydroxy, carboxy, amino and $C_1$–$C_4$ alkoxycarbonyl;

(7') methylthiomethyl, phenylthiomethyl, methylsulphonylmethyl, phenylsulphynylmethyl or phenylsulphonylmethyl;

(8') —$CH_2$—S-Het wherein Het is a heterocyclic ring, preferably chosen from

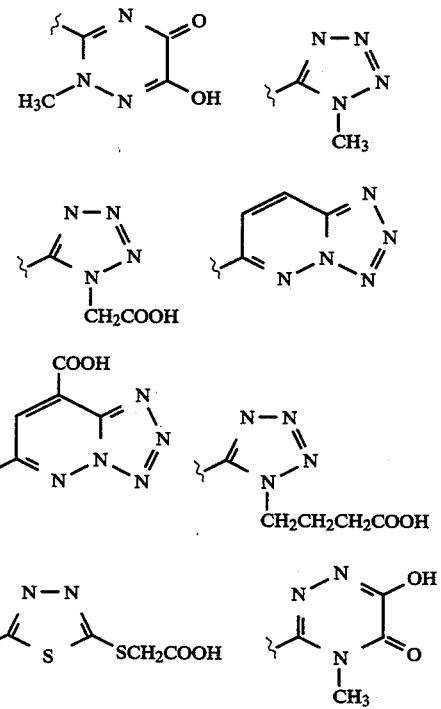

(9') acetoxymethyl, benzoxymethyl, phenylacetoxymethyl or $C_3$–$C_6$ alkanoyloxymethyl, each of which is either unsubstituted or substituted by one or more groups selected from carboxy, hydroxy and $C_1$–$C_3$ alkoxy;

(10') trialkylammoniomethyl, wherein the alkyl group is chosen from methyl, ethyl, propyl, N-methylpyrrolidiniomethyl, N-methylpiperidiniomethyl and N-methylmorpholiniomethyl;

(11') pyridiniomethyl which is either unsubstituted or substituted on the heterocyclic ring by fluoro, chloro, methoxy, hydroxy, carboxy or carbamoyl; or a pharmaceutically or veterinarily acceptable salt thereof.

2. A compound according to claim 1 of the formula (I') in which n is zero, one or two; m is one or two;

A is selected from hydrogen, methyl, ethyl, tert-butyl, neo-pentyl, benzyl, 1-phenylethyl, dimethylphenyl, diphenylmethyl, propenyl, phenylethenyl, cyclopentyl, 1-carboxycyclopentyl, diazomethyl, chloromethyl, hydroxymethyl, methoxymethyl, acetoxymethyl and pivaloyloxymethyl;

B is (1'') methyl, ethyl, propyl, isopropyl, allyl, carboxymethyl, 2-carboxy-2-aminoethyl, cyclopropyl, cyclopentyl, ethoxycarbonylmethyl, 2-carboxyethyl, 2-sulphoethyl or 1,2-dicarboxyethyl;

(2'') phenyl, 2-methoxyphenyl, 3-methoxyphenyl, 4-methoxyphenyl, 4-fluorophenyl, 4-nitrophenyl, 4-hydroxyphenyl, 4-carbamoylphenyl, 4-aminophenyl, 4-acetamidophenyl, 2-acetamidophenyl, 2-carboxyphenyl, 3-carboxyphenyl, 4-carboxyphenyl, 4-benzyhydryloxycarbonylphenyl, 4-tert-butoxycarbonylphenyl, 3-carboxy-4-nitrophenyl, pentafluorophenyl, 4-carboxymethylphenyl or 4-sulphophenyl;

(3'') benzyl, p-carboxybenzyl, p-tert-butoxycarbonylbenzyl, m-carboxybenzyl, o-carboxybenzyl, p-benzhydryloxycarbonylbenzyl or p-sulphobenzyl;

(4'') an heterocyclic ring chosen from:

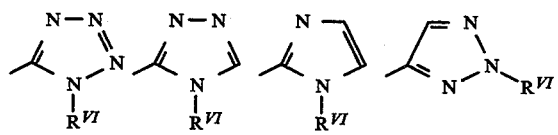

wherein $R^{VI}$ is hydrogen, methyl, carboxymethyl, 2-carboxyethyl, 3-carboxypropyl, 3-benzhydryloxycarbonylpropyl, 2-dimethylaminoethyl, 2-sulphoethyl, ethyl, propyl, phenyl or benzyl;

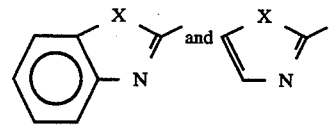

wherein X is oxygen, sulphur or $NR^{VII}$, $R^{VII}$ being hydrogen, methyl, phenyl or carboxymethyl;

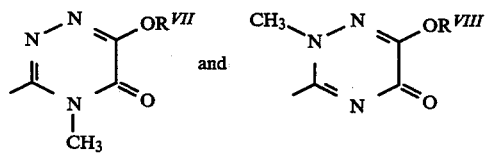

wherein $R^{VIII}$ is hydrogen, methyl, benzyl or benzhydryl; and

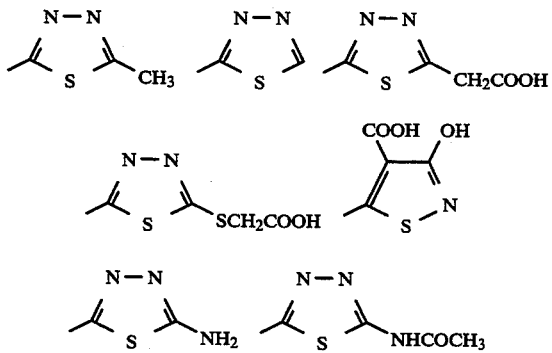

-continued

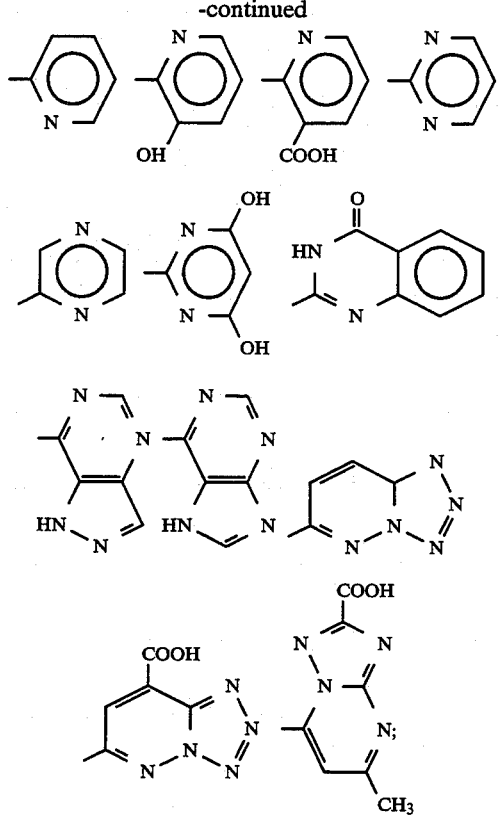

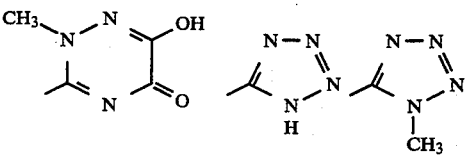
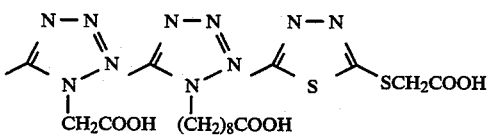
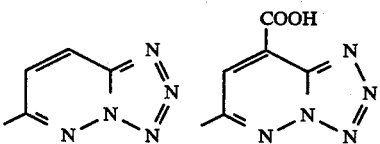
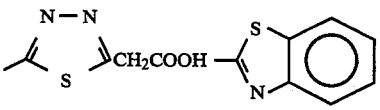

or a pharmaceutically or veterinarily acceptable salt thereof.

R¹ is hydrogen, chloro, bromo, fluoro, methoxy, formamido, acetamido, trifluoroacetamido, methyl, ethyl, propyl, isopropyl, allyl, 1-(hydroxy)ethyl, 1-benzyloxycarbonyloxy)ethyl, 1-(benzoyloxy)ethyl, 1-(phenylacetoxy)ethyl, ethoxy, propoxy, isopropoxy;

R² is hydrogen, methyl, ethyl, bromomethyl, hydroxymethyl, methoxymethyl, carbamoyloxymethyl, carboxy, phenoxymethyl, phenyl, acetoxymethyl, aminomethyl, pyridiniomethyl, benzyloxy-methyl, 3-pyridyloxymethyl, carboxymethoxymethyl, N-carboxy-methylcarbamoyloxymethyl, carboxymethylcarbonyloxymethyl, p-carboxybenzoyloxymethyl, glycyloxymethyl or a CH₂-S-Het group wherein Het is a heterocyclic ring chosen from or a pharmaceutically or veterinarily acceptable salt thereof.

3. A pharmaceutical or veterinary composition comprising a suitable carrier and/or diluent and, as an active principle, a compound according to claim 1 or 2, or a pharmaceutically or veterinarily acceptable salt thereof.

4. A method of treating a mammal suffering from an inflammatory or degenerative disease caused by a proteolytic enzyme, which method comprises administering thereto a therapeutically effective amount of a compound of formula (I') as defined in claim 1 or 2, or a pharmaceutically or veterinarily acceptable salt thereof.

5. A method according to claim 4, wherein the disease is selected from the group consisting of emphysema, adult respiratory distress syndrome, rheumatic fever, spondylitis, gout, lupus and psoriasis.

* * * * *